(12) United States Patent
Marceaux et al.

(10) Patent No.: US 6,210,443 B1
(45) Date of Patent: Apr. 3, 2001

(54) KNEE PROSTHETICS

(75) Inventors: Pascal Marceaux; Jean-François Biegun, both of Chaumont; Jean-Yves Jenny, Lipsheim; Laurent Barba, Ecully; Jacques Hummer, Nancy; Yves Catonne, Le Vauclin; Jean-Paul Barthelemy, Fondettes, all of (FR); Rolf Miehlke, Munster (DE); Dominique Saragaglia, Claix (FR)

(73) Assignee: Aesculap (FR)

( * ) Notice: Subject to any disclaimer, the term of this patent is extended or adjusted under 35 U.S.C. 154(b) by 0 days.

(21) Appl. No.: 09/291,456

(22) Filed: Apr. 14, 1999

(30) Foreign Application Priority Data

Apr. 15, 1998 (FR) .................................................. 98 04665

(51) Int. Cl.⁷ ...................................................... A61F 2/38
(52) U.S. Cl. ...................................... 623/20.33; 623/20.14
(58) Field of Search ............................ 623/20.28, 20.34, 623/20.33, 20.32, 20.31, 20.27, 20.15, 20.16, 20.14, 20.21, 23.41

(56) References Cited

U.S. PATENT DOCUMENTS

| | | | |
|---|---|---|---|
| 4,936,853 | * | 6/1990 | Fabian et al. ........................... 623/20 |
| 4,963,453 | * | 10/1990 | Noesberger et al. ................... 623/20 |
| 5,047,057 | * | 9/1991 | Lawes .................................... 623/20 |
| 5,047,058 | * | 9/1991 | Roberts et al. ......................... 623/20 |
| 5,879,392 | * | 3/1999 | McMinn ................................. 623/20 |

FOREIGN PATENT DOCUMENTS

| | | | |
|---|---|---|---|
| 0 194 326 A1 | 9/1986 | (EP) | .................................. A61F/2/38 |
| 2 676 916 | 12/1992 | (FR) | .................................. A61F/2/38 |
| 2 756 483 | 6/1998 | (FR) | .................................. A61F/2/38 |
| 2 312 166 | 10/1997 | (GB) | .................................. A61F/2/38 |
| WO 95/17860 | 9/1995 | (WO) | ............................... A61F/2/38 |
| WO 98/02116 | 7/1998 | (WO) | ............................... A61F/2/38 |

* cited by examiner

Primary Examiner—Vincent Millin
Assistant Examiner—Alvin Stewart
(74) Attorney, Agent, or Firm—Renner, Kenner, Greive, Bobak, Taylor & Weber

(57) ABSTRACT

Knee prosthetic, incorporating a prosthetic femoral component designed to be fixed to the furthest or nearest extremity, of the femur, a tibial prosthetic component designed to be fixed to the nearest or upper extremity of the tibia and at least one intermediary mobile meniscoid prosthetic involving a lower surface working together by sliding with the complementary upper surface of the tibial component, and at least one upper concave surface working together by sliding with a lower condyloid convex surface of the femoral component, characterised by the fact that the upper surface of the tibial component and the lower surface of the meniscoid component are flat and sloped in the same angle from the top at the rear towards the front.

19 Claims, 3 Drawing Sheets

KNEE PROSTHETICS

FIELD OF THE INVENTION

The present invention relates to knee prosthetics. In particular, the present invention relates to prosthetics that incorporate a femoral prosthetic component designed to be fixed to the furthest or lower extremity of the femur; a tibial prosthetic component designed to be fixed to the nearest or upper extremity of the tibia, and at least one intermediate meniscoid prosthetic component which has at least one upper concave surface which works together with a lower convex condyloid surface of the femoral component, by sliding.

BACKGROUND OF THE INVENTION

Amongst these prosthetics, the invention concerns those which contain a mobile meniscoid component, in contract to those prosthetics in which this meniscoid component is fixed with regard to the tibial component. The mobile meniscoid component can be moved with respect to the tibial component following a general ante-posterior movement, being guided, for example, by a rail, and eventually following an additional limited rotational movement around an axis, which is perpendicular to the direction of the movement.

Amongst these prosthetics incorporating a mobile meniscoid component the invention applies just as well to so-called uni-compartmental ones, that is to say—prosthetics designed to replace the articulation of a single condyle, as to so-called three-compartmental prosthetics, that is to say, prosthetics designed to replace articulation of two condyles, whilst maintaining the rear crossed ligament.

The invention aims to provide a prosthetic of the type which restores the anatomical antero-posterior slope of the upper side of the tibial embase, whilst maintaining maximum preservation of the major bones and simplifying the cut or cut away of the tibia, which is achieved chiefly on a perpendicular plain on the anatomical axis of the tibia.

SUMMARY OF THE INVENTION

According the present invention, there is provided a knee prosthetic, incorporating a femoral prosthetic component designed to be fixed to the furthest or lower extremity of the femur, a tibial prosthetic incorporating an embase of which the lower surface is flat and is designed to lean on a close resection plane of the tibia, and at least one intermediary mobile meniscoid prosthetic component at least in the anteposterior direction and involving a lower surface configured to work together by sliding with one complementary upper surface of the tibial component, and at least one upper concave surface configured to work together by sliding within one lower convex condyloid surface of the femoral component, wherein the upper surface of the tibial component and the lower surface of the meniscoid component are flat and sloping in the same angle from the top at the rear towards the front, with respect to the lower surface of the embase.

Thus, the prosthetic which is the subject of the invention restores not only the anatomical mobility of the menisci, but also the ante-posterior anatomical gradient of the knee, whilst also maintaining the major bones to a maximum and allowing a simple adjustment of the plane of the tibial resection, for example at ninety degrees to the anatomical or mechanical axis of the tibia.

For example, the angle of tilt of these flat surfaces has a value between one and ten degrees, preferably five, with respect to a perpendicular plane to an anatomical axis of the tibia.

Following one method, these two flat surfaces are only inclined in an ante-posterior direction, that is to say, with no gradient in the medio-lateral direction.

Following a second method, these flat surfaces both have a gradient in the medio-lateral direction, the said surfaces being inclined toward the bottom and towards the sagittal or anteposterior plane, of the tibia. In this case, for a three-compartmental type of prosthetic the meniscoid component is in two different parts each one of which may be moved, with regard to the tibial component, at the same time in the ante-posterior direction and invention the medio-lateral such that in the first method, the meniscoid component can be in one part or in two different parts.

In the case of a uni-compartmental prosthetic, the meniscoid component is clearly evident in a single part since it replaces a single natural meniscus.

In both the methods mentioned above, for a three-compartmental prosthetic, the meniscoid component, whether it is made up of a single or two different parts, includes two prosthetic menisci, external and internal both co-operating respectively with two prosthetic condyles, external and internal of the femoral component.

One advantageous characteristic of the invention is that in the case of a three-compartmental prosthetic, the rear edge of upper concave surface of the external prosthetic meniscus is higher than the rear edge of the upper concave surface of the internal prosthetic meniscus, with respect to a perpendicular plane to the tibia axis. This difference in height of the posterior edges of the two prosthetic menisci is between 1 mm and 4 mm, preferably 2 mm.

Another advantageous characteristic of the invention, also in the case of a three-compartmental prosthetic, is that the rear edge of upper concave surface of the external prosthetic meniscus is situated further back than the rear edge of the upper concave surface of the internal prosthetic meniscus, in respect of the medio-lateral plane of the tibia. This distance between the rear waves of the two prosthetic menisci is between 1 mm and 4 mm, preferably 2 mm.

For example, the upper concave meniscoid surface of the meniscoid component and the lower convex condyloid surface of the femoral component are toric surfaces which leads to an arc of a circle being generated.

BRIEF DESCRIPTION OF THE DRAWINGS

FIG. 6 shows a section following line VI—VI of FIG. 5;

DETAILED DESCRIPTION OF THE PREFERRED EMBODIMENTS

Figure 1:
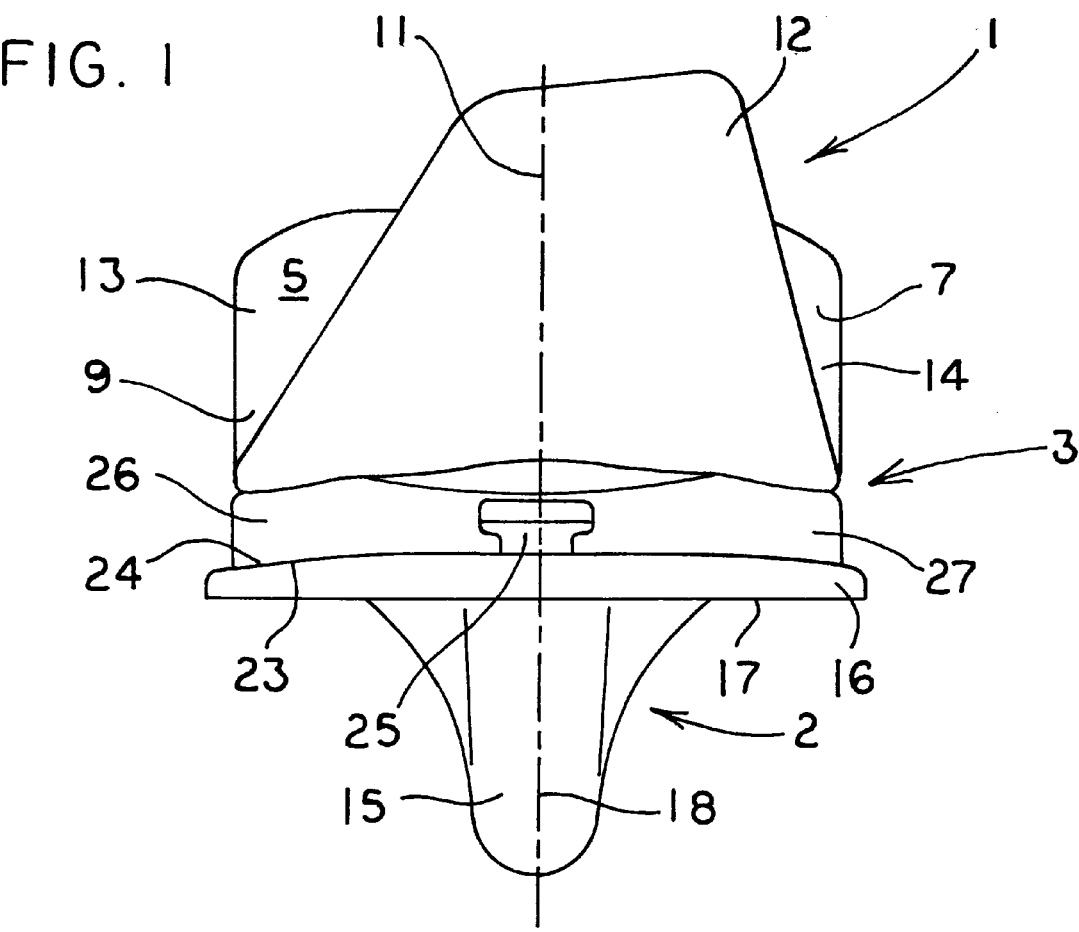
FIG. 1 shows a rear elevation view of a three-compartmental knee prosthetic created whilst following a preferred method of the invention.

A three-compartmental knee prosthetic is shown in the drawings that, incorporates a femoral prosthetic component 1 designed to be fixed to the furthest or lower extremity of the femur; a tibial prosthetic component 2 designed to be fixed to the nearest or upper extremity of the tibia and a mobile meniscoid intermediary prosthetic 3 designed to be used in conjunction with the femoral component 1 and the tibia component 2.

The femoral component 1, in the acknowledged way, is enveloping and it is anchored in the femur by two anchorage blocks 4. Also, the housing where it receives the femur works closely together with the resection surfaces arranged at the furthest extremity of the femur, that is to say one anterior surface 6, one rear surface 7, one far surface 8 and two chamfered surfaces 9 and 10. The far surface 8 is perpendicular to the anatomical or mechanical axis 11 of the femur.

The femoral component 1 is a single part and it has an anterior trochlian part 12 which is connected to its lower part by two condyles 13 and 14.

The tibial component 2 incorporates a ribbed leg for anchorage 15 in the tibia and an embase 18 of the which the lower surface 17 is flat and is designed to lean against a near resection plane arranged on the tibia, perpendicular to its anatomical or mechanical axis 18.

The meniscoid component 3 is in the form of a plateau and it is mobile both with respect to the femoral component 1 and to the tibial component 2.

Figure 4:
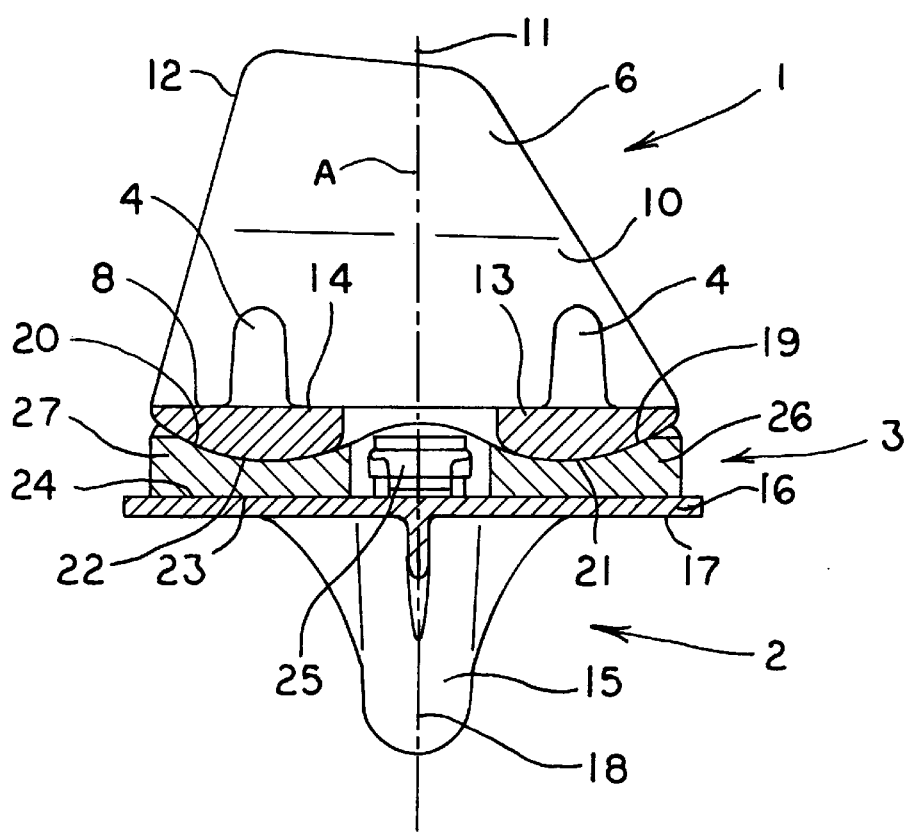
FIG. 4 shows a section following line IV—IV from FIG. 3.
Figure 5:
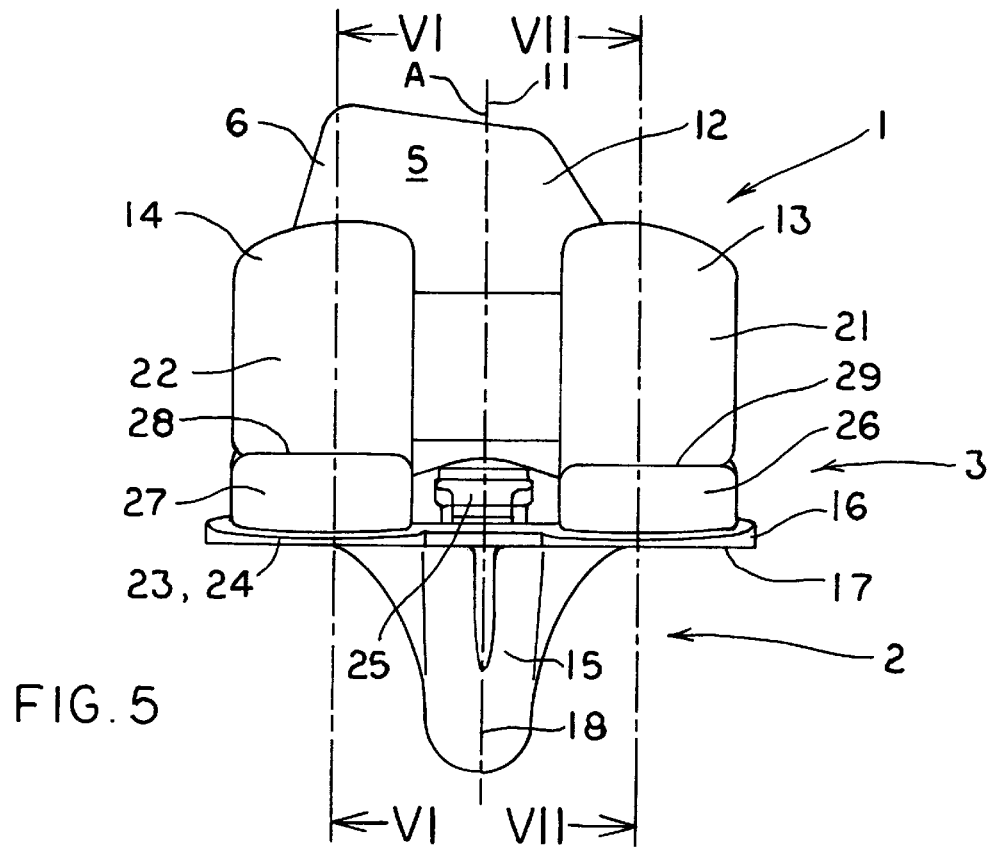
Figures 6, 7:
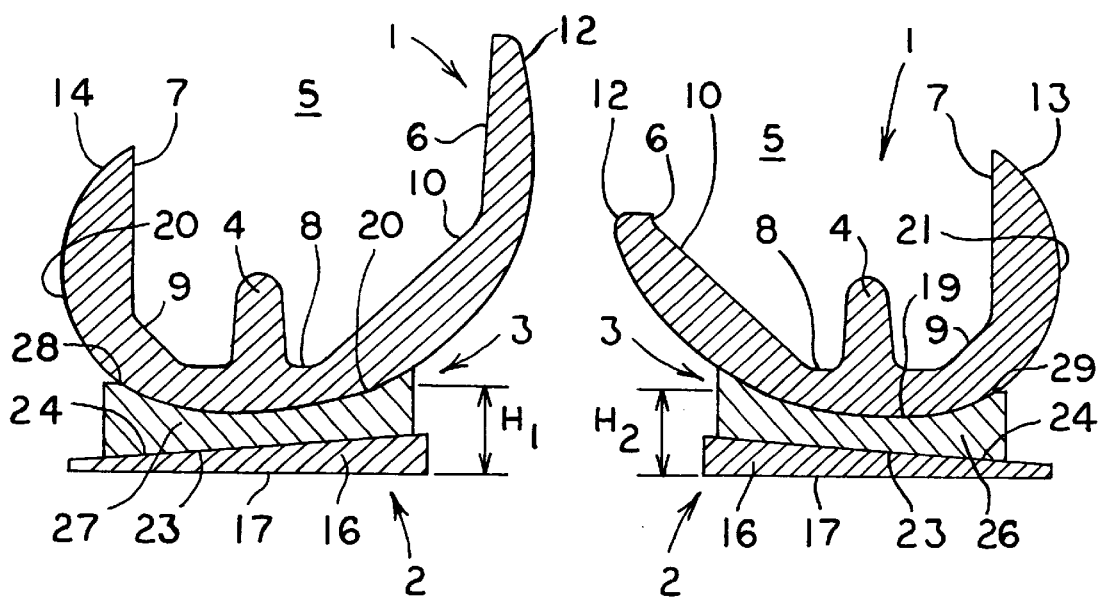
FIG. 6 shows a rear elevation view of the prosthetic from FIG. 1.
FIG. 7 shows a section following line VII—VII of FIG. 6.

By working together with each of the condyles 13 and 14, the meniscoid component 3 has an upper concave surface 19, 20 in the shape of a torus which generates an arc of a circle, which is particularly clear in FIGS. 4, 6 and 7. The axis of the these toric surfaces 19 and 20 is parallel to the medio-lateral direction.

By working together with the toric surfaces 19 and 20, the condyles 13 and 14 have lower convex surfaces 21 and 22 respectively, which are compatible with the concave surfaces 19 and 20, that is to say, that they are also toric.

The type of movement between the femoral component 1 and the meniscoid component 3 is therefore of a sliding roll.

Figure 3:
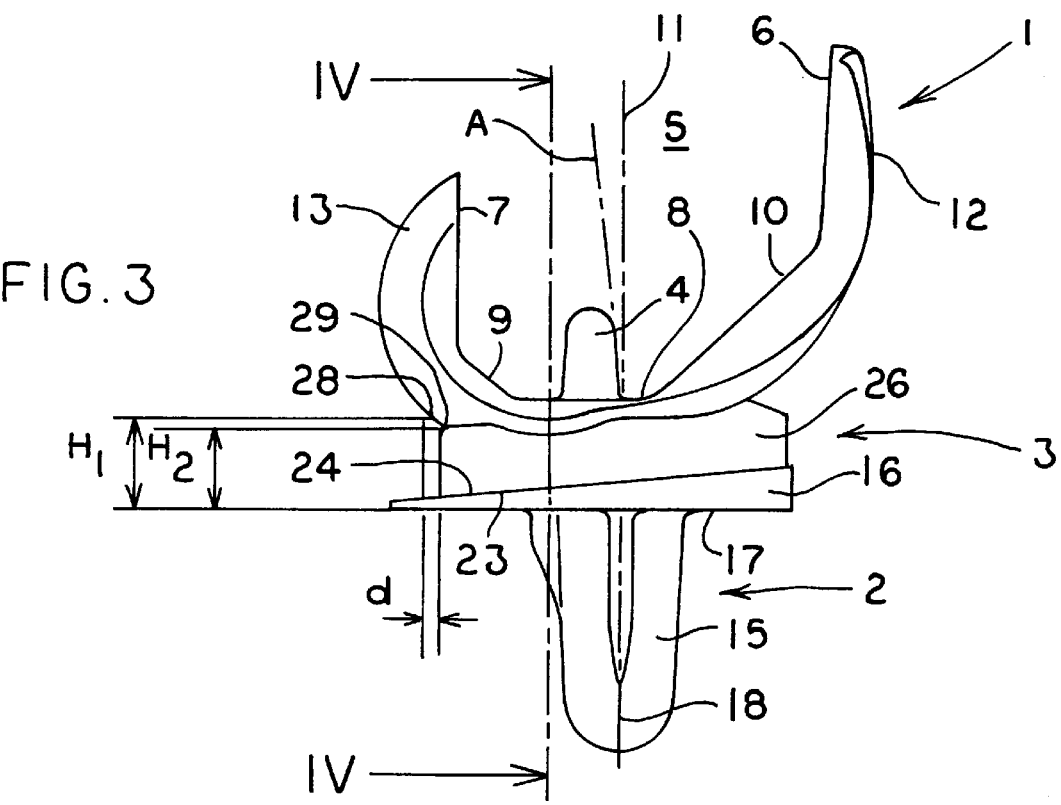
FIG. 3 shows a lateral view from the left of a prosthetic as in FIG. 1.

The meniscoid component 3 combines together with the tibial component 2 by a sliding movement between the flat surfaces of these two components which are inclined at the same angle from the top at the rear towards the front, as can best be seen in FIGS. 3, 6 and 7.

For this combination to work the meniscoid component 3 has a lower flat surface 23 and the tibial component 2 has an upper flat surface 24. In the mode of operation shown, the flat surfaces 23 and 24 are only inclined in the ante-posterior direction of the tibia, that is to day, without sloping in the medio-lateral direction.

The angle of incline of these flat surfaces, with respect to a perpendicular plane to the axis of the tibia, that is to say with respect to the plane of the lower surface 17 of the embase 16, has a favourable value of between one and ten degrees, preferably five degrees.

Following one particular method, not shown here, surfaces 23 and 24 could also have a slope in the medio-lateral direction, being sloped toward the bottom and towards the sagittal or ante-posterior plane of the tibia. In this case, for a three-compartmental prosthetic, each surface 24 is made up of two flat facets in the form of a V and the meniscoid component 3 is in two separate parts which can both be moved about, with respect to the tibial component 2, in both the ante-posterior and medio-lateral direction at the same time.

In the example of the three-compartmental prosthetic shown, in which there is only a slope in the ante-posterior direction, the meniscoid component 3 is better when made up of a single part.

It goes without saying that the meniscoid component 3 can be guided, during its general ante-posterior movement, with respect to the tibial component 2, by any appropriate means as shown in the diagram as item 25, a rail for example, carried by the embase 16. If need be, the rail 25 can turn with respect to embase 16 around an axis situated in the sagittal plane. Should there be only one ante-posterior gradient, this axis is perpendicular to the flat surfaces 23, and 24 so that the meniscoid component has a movement composed of moving around rotation with respect to the tibial component 2. When there is also a medio-lateral gradient, this axis A is perpendicular to the line of intersection of the two flat facets forming the upper surface 24 of the tibial component.

The ante-posterior slope which the sliding surfaces have when the meniscoid component 3 and the tibial component 2 are working together prevents any dislocation, that is to say, a tendency on the part of the meniscoid prosthetic to be thrown forward, after being flexed, which can be carried out with total compatibility between zero and around one hundred and forty degrees.

Another advantage of this ante-posterior slope is the suppression of the movement called "tilting", that is to say the swing of the meniscus under the pressure of the condyle joined to the upheaval of the meniscus in the rear part.

The three-compartmental prosthetic shown in the drawings is asymmetric and, in this case it consists of a prosthetic of a left knee. The corresponding prosthetic for the right knee is symmetric as shown with respect to an ante-posterior plane.

In the configuration shown, the meniscoid component 3 therefore incorporates an internal prosthetic meniscus 26 and an external meniscus prosthetic 27, working with the internal prosthetic condyle 13 and the external prosthetic condyle 14 respectively. As indicated previously, the prosthetic menisci 26 and 27 are made up of one single part and two different parts.

An example of one advantageous characteristic of the invention applicable to this type of three-compartmental prosthetic, is that the risk of dislocation of the external part of the prosthetic is limited, about which it is known that the stability is less than on the internal side, the external condyle 14 providing a surface which works together with the external meniscus 27 which is greater than the surface which works together between the internal condyle 13 and the internal meniscus 26.

Figure 2:
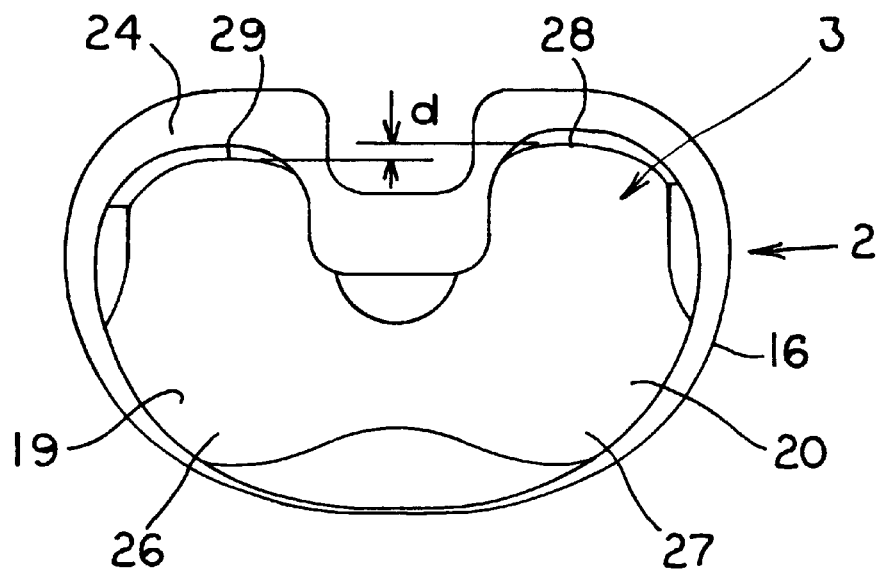
FIG. 2 shows a plan view from above of the prosthetic in FIG. 1 without the femoral prosthetic component.

As can best be seen in FIGS. 2 and 3 this means that the rear edge 28 of the upper concave surface 20 of the external meniscus 27 is situated further back than the rear edge 29 of the upper concave surface 19 of the internal meniscus 26, with respect to the medio-lateral plane. This distance between the rear edges 28 and 29 is represented by d in FIGS. 2 and 3 and has a value of between 1 mm and 4 mm, preferably 2 mm.

This distance between the rear edges of the upper concave surfaces of the menisci 26 and 27 also means, as best shown in FIGS. 3, 5, 6 and 7, that the rear edge 28 of the surface 20 of the external meniscus 27 is higher than the rear edge 29 of the surface 19 of the internal meniscus 26, with respect to a perpendicular plane to the axis of the tibia, that is to say, with respect to the plane of the lower surface 17 of the embase 16 of the tibial component 2.

It can be seen in FIGS. 3, 6 and 7 that, with respect to this plane of reference, height H1 of the rear edge 28 is higher than height H2 of the rear edge 29.

The difference between these two heights has a favourable value of between 1 mm and 4 mm, preferably 2 mm.

In addition, as is seen clearly in FIGS. 3, 6 and 7, because of the ante-posterior slope of the sliding surfaces 23, 24, the meniscoid component 3, the meniscoid component is seen in the form of a corner of which the anterior part is narrower that the rear part.

What is claimed is:

1. A knee prosthetic, incorporating a femoral prosthetic component designed to be fixed to the furthest or lower extremity of the femur, a tibial prosthetic component incorporating an embase of which the lower surface is flat and is designed to lean on a close resection plane of the tibia, and at least one intermediary mobile meniscoid prosthetic component at least in the ante-posterior direction and having a lower surface configured to work together by sliding with one complementary upper surface of the tibial component, and at least one upper concave surface configured to work together by sliding with one lower convex condyloid surface of the femoral component, wherein the upper surface of the tibial component and the lower surface of the meniscoid component are congruent having a flat slope in the same angle from the top at the rear towards the front, with respect to the lower surface of the embase.

2. A prosthetic according to claim 1, wherein the slope of the said flat surfaces is between one degree and ten degrees.

3. A prosthetic according to claim 2, wherein said flat surfaces are only sloping in the ante-posterior direction, with no gradient in the medio-lateral direction.

4. A prosthetic according to claim 2, wherein said flat surfaces include a gradient in the medio-lateral direction, the said surfaces being sloped towards the bottom and towards the sagittal or ante-posterior plane of the tibia.

5. A prosthetic according to claim 4, wherein the meniscoid component is in two different parts each able to move about, with respect to the tibial component, in the ante-posterior direction and in the medio-lateral direction at the same time.

6. A prosthetic according to claim 1, wherein said flat surfaces only slope in the anteposterior direction, with no gradient in the medio-lateral direction.

7. A prosthetic according to claim 1, wherein said flat surfaces include a gradient in the medio-lateral direction, the said surfaces being sloped towards the bottom and towards the sagittal or ante-posterior plane of the tibia.

8. A prosthetic according to claim 7, wherein the meniscoid component is in two different parts each able to move about, with respect to the tibial component, in the ante-posterior direction and in the medio-lateral direction at the same time.

9. A prosthetic according to claim 1, wherein the meniscoid component is in a single part.

10. A prosthetic according to claim 1, wherein said prosthetic is uni-compartmental.

11. A prosthetic according to claim 1, wherein said prosthetic is three-compartmental, the meniscoid component incorporating, in a single part or in two different parts, two prosthetic menisci external and internal working together with two prosthetic condyles external and internal respectively of the femoral component.

12. A prosthetic according to claim 11, wherein the rear edge of the upper concave surface of the external prosthetic meniscus is higher than the rear edge of the upper concave surface of the internal prosthetic meniscus with respect to a perpendicular plane to the axis of the tibia.

13. A prosthetic according to claim 12, wherein the difference in heights of said rear edges is substantially between 1 mm and 4 mm.

14. A prosthetic according to claim 13, wherein said difference in height is substantially 2 mm.

15. A prosthetic according to claim 11, wherein the rear edge of the upper concave surface of the external prosthetic meniscus is situated further back than the rear edge of the upper concave surface of the internal prosthetic meniscus, with respect to the medio-lateral plane of the tibia.

16. A prosthetic according to claim 15, wherein the distance between said rear edges is between 1 mm and 4 mm.

17. A prosthetic according to claim 16, wherein said distance between said rear edges is substantially 2 mm.

18. A prosthetic according to claim 1, wherein the meniscoid component is in the form of a corner of which an anterior part is narrowed with respect to a rear part.

19. A prosthetic according to claim 1, wherein the upper concave meniscoid surface of the meniscoid component and the lower convex condyloid surface of the femoral component are toric surfaces able to generate an arc of a circle.

* * * * *